United States Patent
Gueret

(10) Patent No.: US 6,191,339 B1
(45) Date of Patent: Feb. 20, 2001

(54) THERMAL EFFECT PATCH AND THE USE THEREOF

(75) Inventor: Jean-Louis Gueret, Paris (FR)

(73) Assignee: L'Oreal, Paris (FR)

(*) Notice: Under 35 U.S.C. 154(b), the term of this patent shall be extended for 0 days.

(21) Appl. No.: 09/272,205

(22) Filed: Mar. 19, 1999

(30) Foreign Application Priority Data

Mar. 24, 1998 (FR) .................................................. 98 03588

(51) Int. Cl.⁷ .................................................. A61F 13/00
(52) U.S. Cl. .................................. 602/58; 602/2; 602/43; 602/54
(58) Field of Search ........................ 602/41–59; 128/888, 128/889; 206/440, 441; 428/242, 256, 261, 263

(56) References Cited

U.S. PATENT DOCUMENTS 3,520,403 * 7/1970 Moshel .................................. 206/441
4,619,253 * 10/1986 Anhauser et al. ..................... 602/42

FOREIGN PATENT DOCUMENTS

| 353972 | * | 2/1990 | (EP) . |
| 651984 | * | 5/1995 | (EP) . |
| 2-145854 | | 6/1990 | (JP) . |
| WO 86/00536 | | 1/1986 | (WO) . |

* cited by examiner

Primary Examiner—Kim M. Lewis
(74) Attorney, Agent, or Firm—Oliff & Berridge, PLC

(57) ABSTRACT

The invention relates to a patch for application to the skin. The patch comprises: a reflecting layer that reflects the infrared radiation released by the human body, and between said reflecting layer and said face for application to the skin: a matrix made of a material having self-adhesive properties and comprising at least an acrylic or vinyl polymer whose adhesive properties increase with temperature over the range 20° C. to 40° C.; and in said matrix at least one active substance having an effect on the skin.

19 Claims, 2 Drawing Sheets

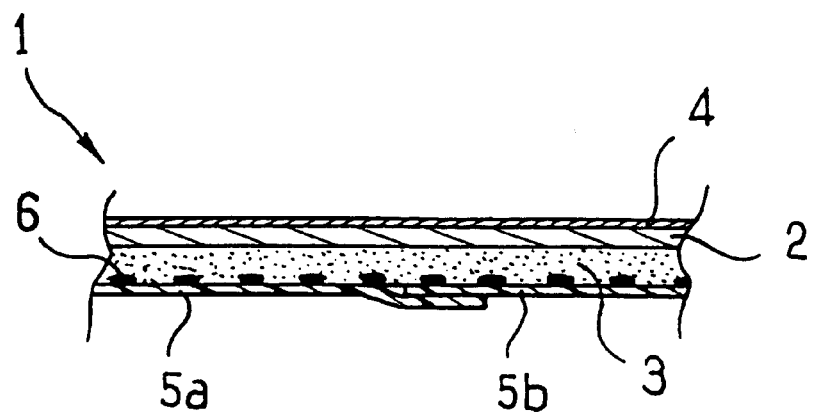
FIG_1
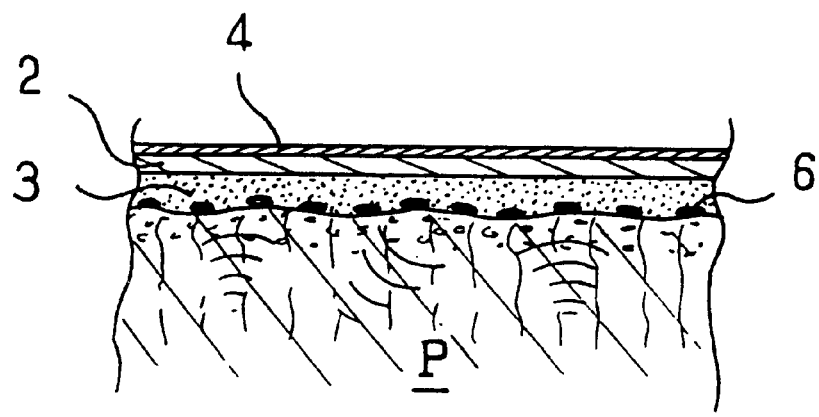
FIG_2

THERMAL EFFECT PATCH AND THE USE THEREOF

The present invention relates to a patch for temporary application to the skin to exert cosmetic and/or pharmaceutical treatment action thereon.

BACKGROUND OF THE INVENTION

Patches are known that comprise a backing sheet coated on one face in a reservoir-forming layer known as a "matrix", containing one or more active substances for diffusing into the skin and/or for acting thereon.

The invention relates more particularly to a patch in which the matrix is made of a material that has intrinsic adhesive properties.

Selecting this material gives rise to difficulties, in particular:

it must be capable of containing the active substance(s) for acting on the skin;

its adhesion to the skin must not be too strong, particularly if it is to be applied in repeated manner, since otherwise the region of the body on which the patch is applied will become irritated and removing the patch will become painful;

its adhesion must not be too weak either, since otherwise it will not be able to adhere to the skin if it is moist or if it becomes moist, e.g. because of sweating;

it must be sufficiently flexible to allow the patch to fit over the shape of the region of the body on which it is applied;

it must remain on the backing sheet when the patch is removed; and finally, it must make it possible to extract the impurities that are to be found on the surface of the skin, in particular sebum or sweat.

In spite of these difficulties, several materials have been proposed for making the matrix, however they are not necessarily suitable for all of the active substances that it might be desirable to incorporate therein.

French patent 2 738 744 or European patent 0 309 309 teach in particular the use of hydrophobic or hyposoluble materials for constituting the matrix.

The hydrosoluble material described in European patent 0 309 309 is relatively impractical in use since it does not present the required adhesive properties prior to application to the skin and it requires the skin to be previously moistened.

OBJECTS AND SUMMARY OF THE INVENTION

The present invention seeks to propose a novel patch whose matrix-constituting material satisfies the requirements listed above and for which diffusion into the skin and/or action on the skin of the active substances contained therein is improved.

The patch of the invention comprises:

a reflecting layer that reflects the infrared radiation released by the human body, and between said reflecting layer and said face for application to the skin:

a matrix made of a material having self-adhesive properties and comprising at least an acrylic or vinyl polymer whose adhesive properties increase with temperature over the range 20° C. to 40° C.; and in said matrix at least one active substance having an effect on the skin.

By means of the invention, the temperature at the interface between the skin and the patch rises quickly, because the thermal radiation released by the body is reflected by the reflecting layer.

This can have multiple advantageous effects, and in particular this can:

significantly increase the temperature of the matrix, and given the particular material selected for making it, reinforce its adhesion to the skin;

enhance diffusion of the active substance(s) within the matrix; and increase blood circulation beneath the patch, which can be favorable to the penetration and/or action of said active substances.

In a particular embodiment of the invention, the matrix is secured to a backing sheet and the reflecting layer is situated on said backing sheet.

Preferably, the reflecting layer is then formed by metallizing at least one of the faces of said backing sheet.

In a particular embodiment of the invention, the patch further comprises a permeable structure such as a net that is embedded at least in part in the matrix so as to modify its overall adhesive power.

In a particular embodiment, the patch further comprises a layer suitable for picking up thermal energy from external radiation.

The invention also provides the use of a patch as specified above for locally reflecting the thermal radiation emitted by the human body and enhancing penetration of an active substance into the skin by a thermal effect.

BRIEF DESCRIPTION OF THE DRAWING

Other characteristics and advantages of the present invention appear on reading the following detailed description of a non-limiting embodiment of the invention, and on examining the accompanying drawing, in which:

FIG. 1 is a diagrammatic section through a patch constituting an embodiment of the invention;

FIG. 2 shows the FIG. 1 patch applied to the skin; and

MORE DETAILED DESCRIPTION

Figure 3:
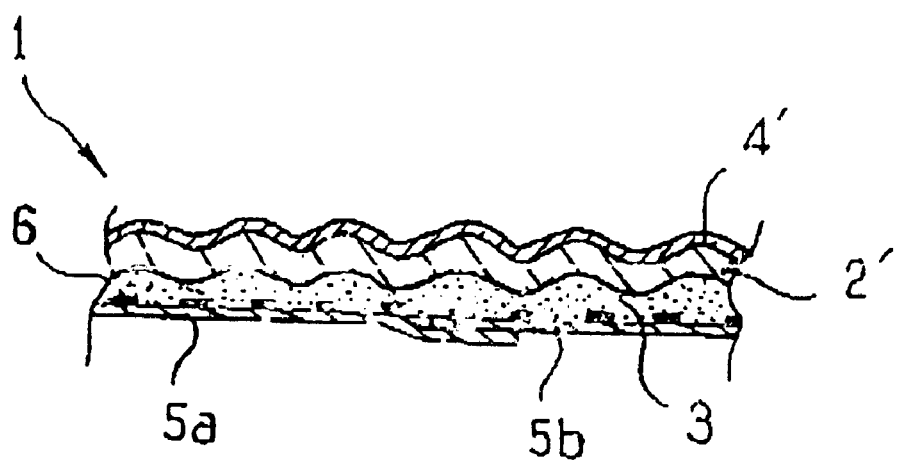
FIG. 3 is a schematic view of an exemplary embodiment of the invention.

FIG. 1 shows a patch 1 constituting an embodiment of the invention, comprising a backing sheet 2 coated on one face with a matrix 3 made of a material having self-adhesive properties.

The backing sheet 2 may have been subjected to corona treatment in order to improve adhesion of the matrix 3.

The backing sheet 2 can be made of a thermally insulating flexible material, e.g. polyester, polyethylene, or polypropylene.

In general, the backing sheet 2 may be made of any other appropriate material, which is optionally occlusive.

On its face that is to be applied to the skin, the matrix 3 is covered by a removable protective membrane, e.g. made of polyethylene containing silicon that is 50 $\mu$m thick.

This protective membrane preferably comprises, as shown in FIG. 1, two portions 5a and 5b which overlap in the middle region of the patch so as to enable the user to remove them without the fingers touching the matrix 3, and thus without causing it to lose any adhesive power.

The patch 1 also has a reflecting layer 4 designed to reflect thermal radiation emitted by the user's body, thereby enabling the matrix 3 to be raised quickly to the temperature thereof.

In the embodiment described, the reflecting layer 4 is made by metallizing the outside face of the backing sheet 2, with the thickness of the backing sheet as metallized in this way lying in the range 10 µm to 120 µm.

The deposited metal may be aluminum, silver, or gold, and the deposited thickness may be selected so that the reflecting layer 4 presents emissivity enabling it specifically to reflect the thermal radiation emitted by the user into the matrix 3.

The thickness of the metal deposit does not spoil the flexibility of the backing sheet 2.

The backing sheet 2 and the matrix 3 come directly into contact with each other over the entire area of their facing faces, and thermal radiation that has passed through the matrix is reflected directly back into it by the reflecting layer.

The entire reflecting layer is useful for reflecting thermal radiation into the adhesive matrix.

In a variant that is not shown, the backing sheet 2 is constituted by metal foil, in particular aluminum foil.

In another variant shown in FIG. 3, the reflecting layer has corrugations that may be the result, for example, of the backing sheet 2 being embossed.

It can also be advantageous to color the matrix 3 and/or the backing sheet 2 with a dark color so as to enable the user, after withdrawing the patch 1, to observed by contrast the quantity and/or the nature of the impurities removed. The user can thus determine whether further application is necessary and also, where appropriate, whether the frequency and/or the nature of the treatment need to be modified.

The material used for making the matrix 3 comprises one or more acrylic or vinyl polymers whose adhesion (measured parallel to the surfaces in contact) preferably lies in the range 50 g/cm² to 800 g/cm² and increases with temperature over the range 20° C. to 40° C.

By way of example, the thickness of the matrix 3 may lie in the range 0.1 mm to 3 mm.

A permeable structure such as a net 6 may be used to modify the overall adhesive power of the matrix 3, as is the case in the example shown in the figures.

Because of the presence of the permeable structure, it is possible to make the matrix out of a material which, in the absence of such a permeable structure, would adhere too strongly to the skin to be suitable for making the desired patch.

By depositing the permeable structure on the surface of the matrix as shown, the area of the matrix that is in contact with the skin is reduced to a multitude of individual zones of small area, such that the overall adhesion on the skin of the matrix-constituting material becomes compatible with use thereof in a patch.

It is easy to decrease or increase adhesion on the skin by an appropriate selection of the permeable structure used, in particular by selecting an appropriate area for its openings.

In a variant that is not shown, it is possible to use a structure that has previously been embedded in the matrix for the purpose of acting on the overall adhesive power of the patch.

The permeable structure used makes it possible, where appropriate, for the active substance(s) contained in the matrix to diffuse towards the surface of the skin.

In another variant that is not shown, it is possible, instead of using a net as the permeable structure to use a non-woven cloth, through which one or more substances contained in the matrix can diffuse, where appropriate.

The non-woven cloth is positioned within the matrix so as to modify the overall adhesive power thereof and obtain the looked-for adhesion.

The adhesion of the matrix could also be modified by making portions in relief on its surface. Such relief can be obtained by means of an embossed protective membrane which, after being removed, leaves the desired relief on the matrix.

The matrix 3 has one or more active substances that have an effect on the skin, e.g. such as, anti-oxidants, free radical scavengers, moisturizers, depigmenting agents, liporegulators, anti-acne agents, anti-dandruff agents, anti-aging agents, softeners, anti-wrinkle agents, keratolytic agents, anti-inflammatory agents, fresheners, healing agents, vascular protectors, antibacterial agents, antifungal agents, antiperspirants, deodorants, skin conditioners, anesthetics, immuno-modulators and nourishing agents, moisture absorbers (cotton, polyacrylate), and sebum absorbers (Orgasol).

The patch of the invention can be manufactured by coating the material that is to constitute the matrix 3 while still soaked in one or more solvents on a conveyor strip that withstands high temperature, and then by causing the entire assembly to pass through an oven for evaporating off the above-mentioned solvent(s).

On leaving the oven, the conveyor strip is separated from the matrix 3 and the matrix is applied to the metallized backing sheet 2, and the assembly is then calendered.

The patch 1 is preferably offered to the user in the pre-cutout state, so as to fit the shape of the region of the body that is to be treated, with the size of the patch lying, for example, in the range 1 cm² to 30 cm².

The patch is advantageously packaged in a protective sachet made up of two sheets of a leakproof laminate of paper and plastics material film, e.g. made of polypropylene, the paper being coated in an adhesive that operates cold.

The sheets are stuck together around the patch by bringing their adhesive-coated faces into contact.

Such packaging has the advantage of protecting the patch from air and of improving conservation thereof.

To use the patch, the user withdraws the protective membrane 5a, 5b and applies the matrix 3 to the skin P, as shown in FIG. 2.

The thermal radiation emitted by the human body is reflected by the reflecting layer 4 back towards the skin P, thereby causing the temperature of the matrix 3 to rise quickly so that it reaches the temperature of the body or a temperature close thereto.

This causes the adhesion of the matrix on the skin to be increased, better diffusion of the active substance(s) contained in the matrix 3, where appropriate, and better penetration thereof into the skin, in particular because of the heat reflected by the patch causing blood vessels to dilate beneath the matrix 3.

Application lasts for a period lying in the range 30 seconds to 5 minutes, for example, and preferably in the range 1 minute to 5 minutes.

Tests have been performed with a patch made by coating a 20 µm thick metallized polyester backing sheet with a matrix comprising an acrylic adhesive based on a solvent (ethyl acetate hexane ethanol), that is self-curing, pressure sensitive, and sold under the name AGXL by MAPEI.

The quantity of adhesive as measured dry and deposited on the backing sheet is 40 g/m².

The matrix 3 also has 1.5% by weight of Kojique's acid, 5% Orgasol powder, 1% healing essence of geranium, and 1% violet pigments sold under the reference DC violet 2K7014 by RDF Chimie.

The initial adhesion of the adhesive used is about 100 g/cm² and its adhesive power (TAC) after being in place for a sufficient length of time is about 300 g/cm².

By using a reflecting layer in accordance with the invention, heat is concentrated and the time required for the adhesive to reach adhesive power close to its maximum adhesive power is considerably reduced.

What is claimed is:

1. A patch having a face for application to the skin, the patch comprising:
    a reflecting layer that reflects infrared radiation released by the human body towards the skin, and between said reflecting layer and said face for application to the skin:
    a matrix made of a material having self-adhesive properties and comprising at least an acrylic or vinyl polymer whose adhesive properties increase with temperature over the range 20° C. to 40° C.; and
    in said matrix at least one active substance having an effect on the skin.

2. A patch according to claim 1, wherein the matrix is secured to a backing sheet and wherein the reflecting layer is situated on said backing sheet.

3. A patch according to claim 2, wherein said reflecting layer is made by metallizing at least one face of the backing sheet.

4. A patch according to claim 3, wherein the reflecting layer has corrugations.

5. A patch according to claim 1, wherein the matrix is covered prior to use by a removable protective membrane having two overlapping portions.

6. A patch according to claim 1, further comprising a permeable structure such as a net embedded at least in part in the matrix so as to modify its overall adhesive power.

7. A patch according to claim 1, wherein the matrix has portions in relief on its face that is to come into contact with the skin.

8. A patch according to claim 1, including a layer having a first surface turned towards the outside of the patch and suitable for picking up thermal energy from external radiation and a second surface turned towards the inside of the patch and suitable for reflecting the infrared radiation released by the human body.

9. A patch according to claim 1, packaged in a protective sachet made up of two sheets of a leakproof laminate of paper and plastics material film, the paper being coated in an adhesive that operates when cold, the sheets being bonded together around the patch by putting faces that are coated in adhesive into contact with each other.

10. A patch according to claim 1, wherein the entire reflecting layer is used for reflecting thermal radiation towards the adhesive matrix.

11. A method of using the patch as defined in claim 1, comprising: locally reflecting thermal radiation emitted by a body and promoting, by a thermal effects, penetration of an active substance into skin of the body.

12. The method according to claim 11, wherein the patch is applied for a duration lying in the range 30 seconds to 5 minutes.

13. The method according to claim 11, wherein the body is a human body.

14. A patch having a face for application to the skin, the patch comprising:
    a reflecting layer that reflects infrared radiation released by the human body towards the skin, and between said reflecting layer and said face for application to the skin:
    a matrix made of a material having self-adhesive properties and comprising at least an acrylic or vinyl polymer whose adhesive properties increase with temperature over the range 20° C. to 40° C.; and
    in said matrix at least one active substance having an effect on the skin;
    said matrix and said reflecting layer being permanently attached.

15. A patch according to claim 14, wherein said matrix is free of any porous material.

16. A patch having a face for application to the skin, the patch comprising:
    a reflecting layer that reflects infrared radiation released by the human body towards the skin, and between said reflecting layer and said face for application to the skin:
    a matrix made of a material having self-adhesive properties and comprising at least an acrylic or vinyl polymer whose adhesive properties increase with temperature over the range 20° C. to 40° C.; and
    in said matrix at least one active substance having an effect on the skin;
    said matrix comprising a permeable structure in the vicinity of said face for application to the skin.

17. A patch having a face for application to the skin, the patch comprising:
    a reflecting layer that reflects infrared radiation released by the human body towards the skin, and between said reflecting layer and said face for application to the skin:
    a matrix made of a material having self-adhesive properties and comprising at least an acrylic or vinyl polymer whose adhesive properties increase with temperature over the range 20° C. to 40° C.;
    in said matrix at least one active substance having an effect on the skin; and
    said reflecting layer consisting of a gold coating.

18. A patch having a face for application to the skin, the patch comprising:
    a reflecting layer that reflects infrared radiation released by the human body towards the skin, and between the reflecting layer and said face for application to the skin:
    a matrix made of material having self-adhesive properties and comprising at least an acrylic or a vinyl polymer whose adhesive properties increase with temperature over the range 20° C. to 40° C.;
    in said matrix at least one active substance having an effect on the skin; and
    said reflecting layer consisting of a silver coating.

19. A patch having a face for application to the skin, the patch comprising:
    a reflecting layer that reflects infrared radiation released by the human body towards the skin, and between said reflecting layer and said face for application to the skin:
    a matrix made of a material having self-adhesive properties and comprising at least an acrylic or vinyl polymer whose adhesive properties increase with temperature over the range of 20° C. to 40° C.;
    in said matrix at least one active substance having an effect on the skin; and
    said reflecting layer consisting of an aluminum coating.

* * * * *